United States Patent
Nakai et al.

(10) Patent No.: US 11,214,545 B2
(45) Date of Patent: Jan. 4, 2022

(54) INDUSTRIAL PROCESS OF MONO-ALKYLATING PIPERIDINE NITROGEN IN PIPERIDINE DERIVATIVE WITH DEUTERATED-LOWER-ALKYL

(71) Applicant: OTSUKA PHARMACEUTICAL CO., LTD., Tokyo (JP)

(72) Inventors: Yuya Nakai, Osaka (JP); Masashi Hayashi, Osaka (JP); Wataru Mitsuhashi, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/644,084

(22) PCT Filed: Sep. 6, 2018

(86) PCT No.: PCT/JP2018/032983
§ 371 (c)(1),
(2) Date: Mar. 3, 2020

(87) PCT Pub. No.: WO2019/049918
PCT Pub. Date: Mar. 14, 2019

(65) Prior Publication Data
US 2020/0407326 A1 Dec. 31, 2020

(30) Foreign Application Priority Data
Sep. 7, 2017 (JP) .............................. JP2017-172351

(51) Int. Cl.
*C07D 221/28* (2006.01)
(52) U.S. Cl.
CPC ................. *C07D 221/28* (2013.01)
(58) Field of Classification Search
CPC ................................................. C07D 221/28
See application file for complete search history.

(56) References Cited

U.S. PATENT DOCUMENTS

| | | |
|---|---|---|
| 2008/0280936 A1 | 11/2008 | Tung |
| 2018/0346498 A1 | 12/2018 | Zhang et al. |
| 2019/0183885 A1 | 6/2019 | Vepachedu et al. |

FOREIGN PATENT DOCUMENTS

| | | |
|---|---|---|
| CN | 108675959 A | 10/2018 |
| CN | 110028433 A | 7/2019 |
| JP | 2014-520140 A | 8/2014 |
| JP | 2018-536667 A | 12/2018 |
| WO | 2008/137474 A1 | 11/2008 |
| WO | 2012/176066 A1 | 12/2012 |
| WO | 2018/039642 A1 | 3/2018 |
| WO | 2019/049918 A1 | 3/2019 |

OTHER PUBLICATIONS

Ian Fellows et al, "Simple methods for the labelling of N-methyl amines using isotopically labelled methyl iodide", Journal of Labelled Compounds and Radiopharmaceuticals, John Wiley, GB, vol. 41, No. 12, Jan. 1, 1998 (Jan. 1, 1998), pp. 1127-1143 (17 pages).
Hedvig Bölcskei et al., "Synthesis of deuterated dextromethorphan derivatives", ARKIVOC, vol. 3, Jan. 1, 2008 (Jan. 1, 2008), pp. 182-193 (12 Pages).
Heinkele G et al., "Synthesis of [$^2H_3$]-dextromethorphan and its major urinary metabolites [$^2H_3$]-dextrorphan and [$^2H_3$]-dextrorphan-β-glucoronide", Journal of Labelled Compounds and Radiopharmaceuticals, John Wiley, GB, vol. 45, Jan. 1, 2002 (Jan. 1, 2002), pp. 1153-1158 (6 Pages).
International Search Report in International Application No. PCT/JP2018/032983, dated Nov. 7, 2018.
International Preliminary Report on Patentability with Written Opinion in International Application No. PCT/JP2018/032983, dated Mar. 10, 2020.
International Search Report dated Apr. 21, 2020 in International Application No. PCT/JP2020/010873.
International Preliminary Report on Patentability dated Sep. 23, 2021 with a Translation of the Written Opinion of the International Searching Authority in Application No. PCT/JP2020/010873.

*Primary Examiner* — Bruck Kifle
(74) *Attorney, Agent, or Firm* — Sughrue Mion, PLLC

(57) ABSTRACT

The present invention relates to a method of mono-alkylating a piperidine nitrogen in a piperidine derivative with a deuterated lower-alkyl, which comprises protecting the piperidine nitrogen with an aralkyl protective group, lower-alkylating the piperidine nitrogen with a deuterated-lower-alkylating agent under neutral or basic condition, and then deprotecting the aralkyl protective group.

12 Claims, No Drawings

INDUSTRIAL PROCESS OF MONO-ALKYLATING PIPERIDINE NITROGEN IN PIPERIDINE DERIVATIVE WITH DEUTERATED-LOWER-ALKYL

CROSS REFERENCE TO RELATED APPLICATIONS

This application is a National Stage of International Application No. PCT/JP2018/032983 filed Sep. 6, 2018, claiming priority based on Japanese Patent Application No. 2017-172351 filed Sep. 7, 2017.

TECHNICAL FIELD

The present invention relates to a method of mono-alkylating a piperidine nitrogen in a piperidine derivative with a deuterated lower-alkyl, in more detail, a method of replacing N-methyl in dextromethorphan by N-($d_3$-methyl).

BACKGROUND ART

Dextromethorphan is a drug of the morphinan class with sedative and dissociative properties, having the chemical structure shown below, which is broadly used as an antitussive and expectorant agent.

[Chem. 1]

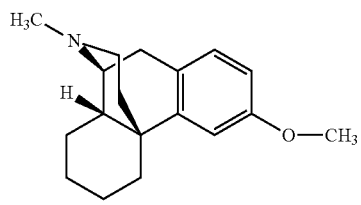

Dextromethorphan is metabolized in the liver. Recently, it is expected that a metabolic change of dextromethorphan in the liver could bring in the sustained action, the reduction of side-effect, the induction of a new useful action, etc., and actually the studies thereof have been started. In particular, considering that the metabolism of dextromethorphan starts with the elimination of O-methyl and N-methyl, it has been studied to give a change to the metabolism by replacing these methyl groups with deuterated methyl groups (Patent Literature 1).

As a method of replacing N-methyl in dextromethorphan with N-($d_3$-methyl), first the N-methyl group is eliminated, and then N-($d_3$-methyl) group is introduced there with a $d_3$-methylating agent, which is the most typical method. For example, Non Patent Literature 1 succeeded in preparing dextromethorphan having N-($d_3$-methyl) in laboratory scale by reacting N-desmethyl-dextromethorphan in the presence of sodium hydride in THF with $CD_3I$ which is a $d_3$-methylating agent. However, the production method was not a practicable one, because sodium hydride used therein is a strong base which can be easily and vigorously reacted with water to generate hydrogen gas, and if the production method is carried out in industrial scale, it is absolutely necessary to make the reaction with completely-dehydrated solvents under inactive gas from the viewpoint of safety. In addition, it is generally difficult to control the N-monoalkylation on the amino site of N-desmethyl-dextromethorphan, i.e., the alkylation is apt to over-proceed to produce N-dialkylated product as an impurity. Thus, the above-mentioned general method of N-alkylation has had a problem of low purity or low yield, in particular, for the reaction with an expensive $d_3$-methylating agent, such low yield has been a big problem in industrial process.

[Chem. 2]

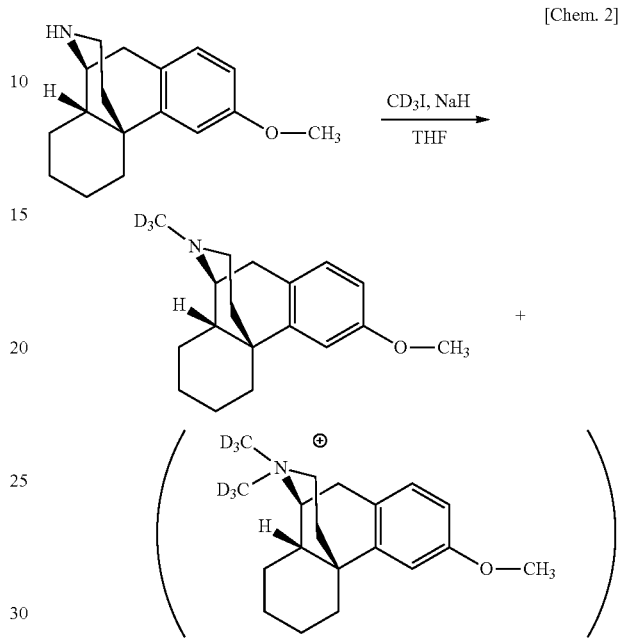

As the $d_3$-methylation, another method has been known, in which N-desmethyl-dextromethorphan can be $d_3$-methylated without $d_3$-methylating agent (Patent Literature 1, Non Patent Literature 2). According to the alternative method, first the nitrogen site of N-desmethyl-dextromethorphan is carbamate-modified with ethyl chloroformate and then reduced with $LiAlD_4$ which is a deuterium source to prepare N-($d_3$-methyl) dextromethorphan, which can suppress the overreaction to N-dialkylated product. However, the deuteration with $LiAlD_4$ can fail to replace all hydrogen atoms with deuterium, i.e., it can produce 17-$CHD_2$ form. It is a severe problem of lowered deuteration rate.

[Chem. 3]

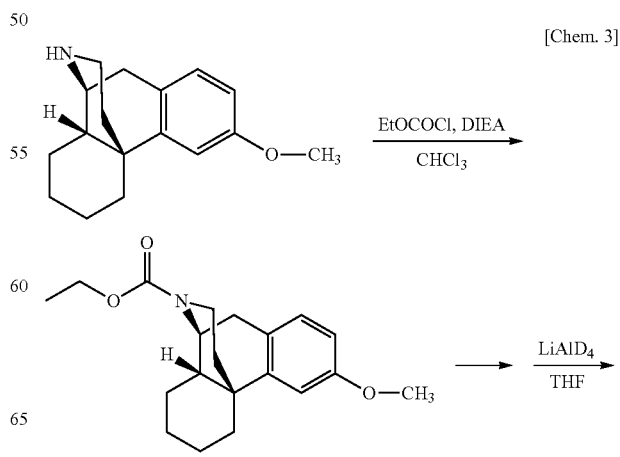

-continued

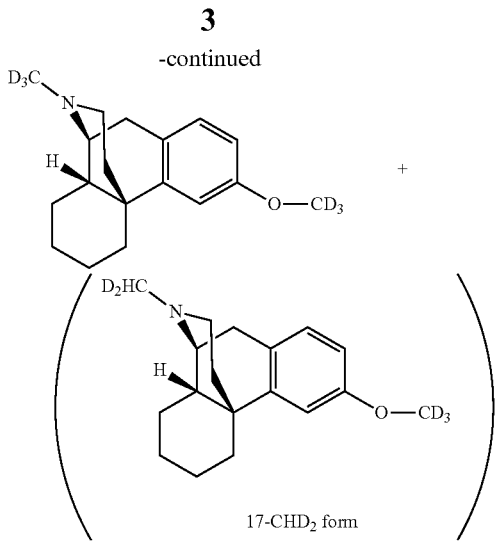

17-CHD$_2$ form

CITATION LIST

Patent Literature

[PL 1] WO 2008/137474

Non Patent Literature

[NPL 1] ARKIVOC 2008 (iii) 182-193
[NPL 2] J Label Compd Radiopharm 2002, 45, 1153-1158

SUMMARY OF INVENTION

Technical Problem

As mentioned above, in order to replace the N-methyl in dextromethorphan with N-(d$_3$-methyl) by an industrial process, it is necessary to suppress producing such by-product as much as possible, but in fact there has not been useful industrial method.

Solution to Problem

The present inventors have extensively studied and then have found that the desired deuterated dextromethorphan can be prepared without producing the bothersome by-product, by temporarily protecting the amine nitrogen in N-desmethyl-dextromethorphan with an aralkyl protective group such as benzyl group, deuterated-methylating the nitrogen in the aralkyl-protected dextromethorphan with a deuterated-methylating agent under neutral or basic condition to produce its quaternary amine product, and then deprotecting the aralkyl protective group. Based upon the new findings, the present invention has been completed. The present technique is thought to be also applicable in the nitrogen part in a general piperidine derivative, like the deuterated-lower-alkylation of the nitrogen in N-desmethyl-dextromethorphan.

The present invention includes the following embodiments. (Term 1) A method of mono-alkylating a piperidine nitrogen in a piperidine derivative with a deuterated lower-alkyl by
protecting the piperidine nitrogen with an aralkyl protective group,
lower-alkylating the piperidine nitrogen with a deuterated-lower-alkylating agent under neutral or basic condition, and then
deprotecting the aralkyl protective group.

(Term 2) The method of Term 1, wherein the piperidine derivative is a morphinan derivative.

(Term 3) The method of Term 2, wherein the morphinan derivative is N-desmethyl form of dextromethorphan (i.e., 3-methoxymorphinan).

(Term 4) The method of any one of Terms 1-3, wherein the mono-alkylation is mono-methylation or mono-ethylation, and the deuterated-lower-alkylating agent is deuterated-methylating agent or deuterated-ethylating agent.

(Term 5) The method of any one of Terms 1-3, wherein the mono-alkylation is mono-methylation, and the deuterated-lower-alkylating agent is [$^2$H$_3$]methyl methanesulfonate, [$^2$H$_3$]methyl benzenesulfonate, [$^2$H$_3$]methyl 4-methylbenzenesulfonate, [$^2$H$_3$]methyl 2-nitrobenzenesulfonate, [$^2$H$_3$]methyl 4-nitrobenzenesulfonate, di-[$^2$H$_3$]methyl sulfate, di-[$^2$H$_3$]methyl carbonate, [$^2$H$_3$]methyl trifluoromethanesulfonate, [$^2$H$_3$]methyl bromide, or [$^2$H$_3$]methyl iodide.

(Term 6) The method of any one of Terms 1-5, wherein the aralkyl protective group is a benzyl-derivative protective group.

(Term 7) The method of Term 6, wherein the benzyl-derivative protective group is benzyl protective group.

(Term 8) The method of Term 6 or 7, wherein the deprotection is to deprotect the benzyl-derivative protective group by hydrogenation.

(Term 9) The method of any one of Terms 1-8, wherein the basic condition is adjusted with sodium carbonate, cesium carbonate, potassium carbonate, sodium bicarbonate, potassium bicarbonate, sodium hydride, potassium hydride, sodium hydroxide, potassium hydroxide, sodium tert-butoxide, potassium tert-butoxide, alkyllithium (e.g. n-butyllithium, sec-butyllithium, tert-butyllithium, n-hexyllithium), lithium amide (e.g. lithium diisopropyl amide, lithium hexamethyldisilazide), sodium methoxide, or tert-amine (e.g. trimethylamine, triethylamine, triisopropylamine, diisopropylethylamine).

(Term 10) A method of preparing 3-(methoxy-d$_3$)-17-(methyl-d$_3$)-morphinan from 3-methoxymorphinan by the method of any one of Terms 3-9, wherein
the methoxy group at the 3rd position of the morphinan is transformed to hydroxy group under acidic condition or Lewis acidic condition after protecting the piperidine nitrogen with an aralkyl protective group, and
followed by the deuterated-lower-alkylation and the deprotection.

Effect of Invention

The present invention makes it possible to deuterated-monomethylate the piperidine nitrogen in a morphinan derivative, particularly 3-methoxymorphinan, effectively with deuterated methyl, by temporarily protecting the piperidine nitrogen with an aralkyl protective group such as benzyl group, deuterated-methylating the nitrogen in the aralkyl-protected morphinan derivative with a deuterated-methylating agent, and then deprotecting the aralkyl protective group, which does not produce a by-product that is di-methylated with deuterated methyl. In addition, 3-(methoxy-d$_3$)-17-(methyl-d$_3$)-morphinan can be efficiently prepared by protecting the piperidine nitrogen with an aralkyl protective group, transforming the methoxy group at the 3rd position of the morphinan to hydroxy group under acidic condition or Lewis acidic condition, deuterated-methylating the hydroxy group, and then deprotecting the above protective group. Furthermore, the technique of the present invention can be applied in the reaction with not only a deuterated-methylating agent, but also a deuterated-lower-alkylating agent, and it can be also applied in the deuterated-lower-alkylation of the nitrogen site in a general piperidine derivative in the same way as 3-methoxymorphinan.

The present invention can suppress the production of a by-product, thus the used amount of the expensive $d_3$-methylating agent can be reduced, i.e., the industrial manufacture cost can be reduced. [$^2H_3$]Methyl methanesulfonate and [$^2H_3$]methyl benzenesulfonate which can be used as a $d_3$-methylating agent in the present invention can be prepared from highly pure deuterated methanol ($CD_3OD$, $d_4$-methanol) which is widely used as deuterium source, thus it is expected to bring in further costcut. In addition, deuterated methanol which is a starting material of the deuterated-methylating agent having sulfonate group is highly safe in handling such as carriage since deuterated methanol has no mutagenesis like $CD_3I$.

DESCRIPTION OF EMBODIMENTS

The term "morphinan derivative" used herein denotes morphinan itself which has the structure shown below and various derivatives thereof which have similar structure to morphinan, which also includes their salt thereof. These compound groups may have various substituents at any sites other than the piperidine nitrogen, which include, for example, N-desmethyl form of dextromethorphan (3-methoxymorphinan), N-desmethyl form of dimemorfan (3-methylmorphinan), N-desmethyl form of dextrorphan (3-hydroxymorphinan), N-desmethyl form of drotebanol, and N-desmethyl form of sinomenine. Here, the piperidine nitrogen means the secondary amine of the nitrogen atom site at the piperidine ring in the compound.

[Chem. 4]

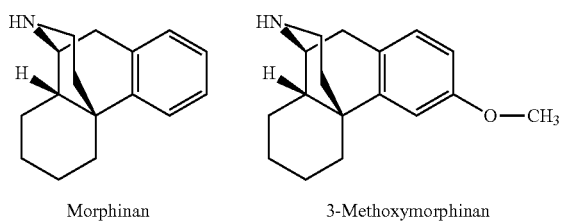

Morphinan      3-Methoxymorphinan

The term "aralkyl protective group" used herein for protecting a piperidine nitrogen denotes a protective group having an alkyl group wherein one of hydrogen atoms in the alkyl group is replaced by an aryl group, which includes, for example, a protective group having benzyl-derivative, in more detail, benzyl group, 4-nitrobenzyl group, 4-methoxybenzyl group, 2-nitrobenzyl group, 4-chlorobenzyl group, 2,6-dichlorobenzyl group, 4-methylbenzyl group, and 2,4,6-trimethylbenzyl group. Preferably, it is benzyl group.

Exemplified methods to introduce such aralkyl protective group to a piperidine nitrogen include methods disclosed in T. W. Greene and P. G. M. Wuts, "Greene's Protective Groups in Organic Synthesis", 4th edition, Wiley, New York 2006, or similar methods. For example, they include a method of treating with a halogenated benzyl in the presence of a base, and a reductive amination in which a piperidine nitrogen is reacted with a benzaldehyde compound to give its imine compound which is reduced with a reducing agent such as sodium borohydride, cyanosodium borohydride, and sodium triacetoxyborohydride.

The deprotection of an aralkyl group may be also carried out according to methods disclosed in T. W. Greene and P. G. M. Wuts, "Greene's Protective Groups in Organic Synthesis", 4th edition, Wiley, New York 2006, or similar methods. For example, for benzyl group or p-methoxybenzyl group, the protecting group can be removed by hydrogenation with palladium catalyst, or under a mild acidic condition with DDQ, CAN, or the like.

The term "mono-lower-alkylation with a deuterated-lower-alkyl" used herein denotes substituting with one lower alkyl group wherein one or more of hydrogen atoms in the alkyl group are replaced by deuterium. The lower alkyl part includes, for example, methyl and ethyl, preferably methyl. And, regarding methyl or ethyl, it is preferable that all hydrogen atoms in the alkyl group are replaced by deuterium, which includes, for example, [$^2H_3$]methyl and [$^2H_5$]ethyl. In the present invention, a methyl group wherein all the three hydrogen atoms are replaced by deuterium denotes, for example, [$^2H_3$]methyl, $d_3$-methyl, methyl-$d_3$, deuterated methyl, and $CD_3$.

The "deuterated-lower-alkylating agent" has a structure that deuterated-lower-alkyl group is combined with a suitable leaving group, wherein the deuterated-lower-alkyl group includes the above-mentioned ones; and the leaving group includes, preferably, halogen group (such as iodo and bromo), sulfonate group (such as methanesulfonate group, benzenesulfonate group, 4-methylbenzenesulfonate group, group, and trifluoromethanesulfonate group), as well as sulfate group and carbonate group which are bivalent leaving groups bindable to two alkyl groups.

The deuterated-lower-alkylating agent includes, for example, [$^2H_3$]methyl methanesulfonate, [$^2H_3$]methyl benzenesulfonate, [$^2H_3$]methyl 4-methylbenzenesulfonate, [$^2H_3$]methyl 2-nitrobenzenesulfonate, [$^2H_3$]methyl 4-nitrobenzenesulfonate, di-[$^2H_3$]methyl sulfate, di-[$^2H_3$]methyl carbonate, [$^2H_3$]methyl trifluoromethanesulfonate, [$^2H_3$]methyl bromide, and [$^2H_3$]methyl iodide, preferably [$^2H_3$]methyl iodide and [$^2H_3$]methyl sulfonate group (in particular, [$^2H_3$]methyl 4-methylbenzenesulfonate).

Among the "deuterated-lower-alkylating agent", an alkylating agent including sulfonate group can be prepared by a conventional method with, for example, deuterated methanol. As shown in the reference example below, for example, it can be prepared by reacting sulfonyl chloride reagent and deuterated methanol under basic condition.

The deuterated-lower-alkylation of a piperidine nitrogen can be achieved by reacting a piperidine derivative and a deuterated-lower-alkylating agent in an inert solvent under neutral or basic condition. The "neutral condition" used herein means pH condition made naturally from starting materials, reagents, solvents, and the like, i.e., which is pH condition made without any specific pH adjustment, or pH condition adjusted to around neutral by adding reagents which are mentioned in the following basic condition. The pH means, for example, about 6-8, preferably 6.5-7.5. The "basic condition" used herein includes basic condition adjusted with sodium carbonate, cesium carbonate, potassium carbonate, sodium bicarbonate, potassium bicarbonate, sodium hydride, potassium hydride, sodium hydroxide, potassium hydroxide, sodium tert-butoxide, potassium tert-butoxide, alkyllithium (such as n-butyllithium, sec-butyllithium, tert-butyllithium, and n-hexyllithium), lithium amide (such as lithium diisopropyl amide, and lithium hexamethyldisilazide), sodium methoxide, or tert-amine (such as trimethylamine, triethylamine, triisopropylamine, and diisopropylethylamine), preferably sodium carbonate, cesium carbonate, potassium carbonate, sodium bicarbonate, and potassium bicarbonate, particularly preferably sodium bicarbonate. These basic compounds may be used singly or in combination of plural compounds. The used amount of the basic compound is generally about 1 mole-10 moles, preferably about 1 mole-6 moles, per mole of starting material.

As shown in the following scheme, it is thought that the piperidine nitrogen is deuterated-lower-methylated to give its quaternized amine in the reaction of the present invention, but preferably the produced quaternized amine compound is forwarded to the next step without isolation, i.e., deprotecting the aralkyl group to give the desired product that is mono-lower-alkylated with deuterated methyl.

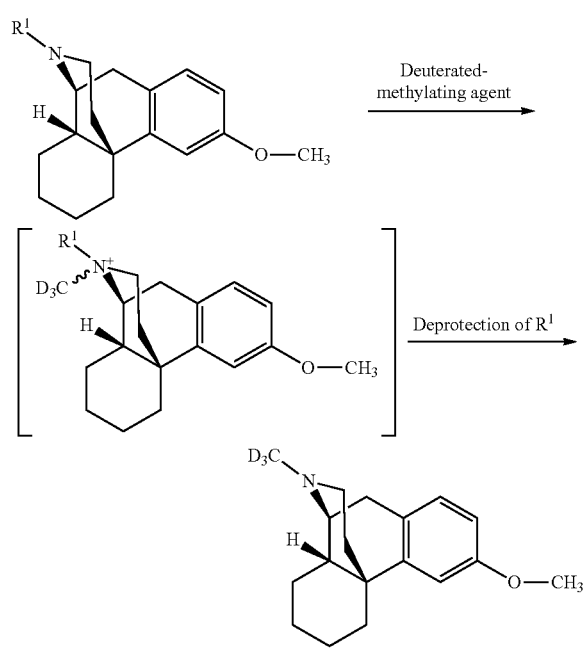

[Chem. 5]

Wherein $R^1$ is an aralkyl protective group such as benzyl.

In addition, as shown in the following scheme, for example, 3-methoxy-morphinan derivative may be reacted in an inert solvent under acidic condition or in the presence of Lewis acid to transform the methoxy group at the 3rd position to hydroxy group, and then the hydroxy group may be also deuterated-lower-alkylated when the piperidine nitrogen is deuterated-lower-alkylated. When the hydroxy group is simultaneously deuterated-lower-alkylated, it is preferable that the reaction is done, not under neutral condition, but under basic one. The acidic condition in the reaction of transforming the methoxy group at the 3rd position to hydroxy group may be adjusted with hydrobromic acid or the like, and the Lewis acid includes boron tribromide.

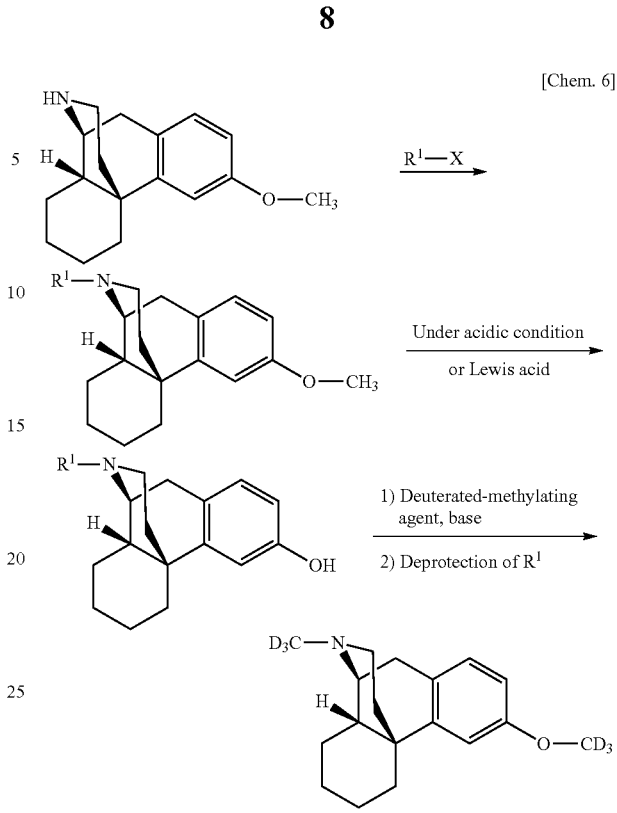

[Chem. 6]

Wherein $R^1$ is an aralkyl protective group such as benzyl, X is halogen such as Cl.

The above-mentioned reactions of the present invention may be done in an inert solvent. Said inert solvent can be chosen suitably depending on the reaction condition, which includes, for example, water; an ether type solvent such as dioxane, tetrahydrofuran, diethyl ether, 1,2-dimethoxyethane, diethylene glycol dimethyl ether, and ethylene glycol dimethyl ether; an aromatic hydrocarbon type solvent such as benzene, toluene, and xylene; a lower alcohol type solvent such as methanol, ethanol, and isopropanol; a ketone type solvent such as acetone and methyl ethyl ketone; and a polar solvent such as N,N-dimethylformamide (DMF), N,N-dimethylacetamide (DMA), dimethylsulfoxide (DMSO), hexamethylphosphoric triamide, and acetonitrile. The inert solvent may be a single solvent or a mixture of two or more solvents.

The above-mentioned reactions of the present invention may be done under ordinary pressure or increased pressure, under an inert gas atmosphere such as nitrogen and argon. The above-mentioned reactions are done usually at room temperature to at 200° C., preferably at room temperature to at 150° C., and are completed generally in about 1-30 hours.

In the present invention, the starting materials, intermediates, and/or desired compounds may be their salt compounds thereof, and the present invention also encompasses processes including such salt compounds. The salt compounds can be in acid addition salt form, or sometimes in salt form with a base, depending on the type of substituents. Said acid includes, for example, an inorganic acid such as hydrochloric acid, hydrobromic acid, nitric acid, sulfuric acid, phosphoric acid; and an organic acid such as methanesulfonic acid, p-toluenesulfonic acid, acetic acid, oxalic acid, citric acid, tartaric acid, maleic acid, fumaric acid, malic acid, and lactic acid. Said base includes, for example, an inorganic base such as sodium hydroxide, potassium hydroxide, calcium hydroxide, sodium carbonate, potassium carbonate, sodium bicarbonate, and potassium bicarbonate; and an organic base such as methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, and choline; and additionally an ammonium salt. And, said salt may be a salt with an amino acid such as lysine, arginine, aspartate, and glutamate.

EXAMPLES

The present invention is explained in more detail in the following by referring to Reference examples and Examples, however, the present invention should not be limited thereto. Each "UPLC Purity" shown in Reference examples and Examples was measured with Acquity Ultra Performance LC of Waters.

Synthesis of $d_3$-Methylating Agent from $d_4$-Methanol

[Chem. 7]

Wherein $R^2$ is methyl, phenyl, 4-methylphenyl, 2 nitrophenyl, or 4-nitrophenyl.

Each $d_3$-methylating agent wherein $R^2$ is each of the above-listed ones was prepared in the following Reference examples 1-5.

Reference Example 1

Synthesis of [$^2H_3$]methyl Methanesulfonate $d_4$-Methanol (5.0 mL) and triethylamine (25.7 mL) were dissolved in dichloromethane (123 mL), and the solution was cooled at −30° C. To the cooled solution was added dropwise a solution of methanesulfonyl chloride (10.6 mL) in dichloromethane (20 mL), and the solution was stirred at −30° C. for 3 hours. The solution was warmed to 0° C., and purified water (150 mL) was added thereto. The organic layer was separated, washed with 1 N hydrochloric acid (50 mL) and saturated aqueous sodium bicarbonate (50 mL), and dried over anhydrous sodium sulfate. The solvent was removed in vacuo from the obtained solution to give the titled compound as a colorless oil (9.27 g, Yield: 66%).
$^1$H-NMR (300 MHz, CDCl$_3$) δ: 3.02 (3H, s).

Reference Example 2

Synthesis of [$^2H_3$]methyl Benzenesulfonate

Benzenesulfonyl chloride (26.1 g) and $d_4$-methanol (5.0 mL) were dissolved in toluene (200 mL), and the solution was cooled below 0° C. To the cooled solution was added dropwise 48% aqueous sodium hydroxide (30 mL) with care to prevent the temperature from rising over 10° C., and the solution was stirred below 10° C. for 30 minutes. Then, the solution was warmed and stirred for one hour but not over 30° C., and further warmed and stirred at 40° C. for two hours. Purified water (75 mL) was added thereto. The organic layer was separated, washed with purified water (50 mL) three times, and dried over anhydrous sodium sulfate. The solvent was removed in vacuo from the obtained solution to give the titled compound as a colorless oil (21.1 g, Yield: 97.4%, UPLC Purity: >99%).
$^1$H-NMR (300 MHz, CDCl$_3$) δ: 7.55-7.61 (2H, m), 7.65-7.71 (1H, m), 7.91-7.95 (2H, m).

Reference Example 3

Synthesis of [$^2H_3$]methyl 4-methylbenzenesulfonate

4-Toluenesulfonyl chloride (282 g) and $d_4$-methanol (50 mL) were dissolved in toluene (1.0 L), and the solution was cooled below 0° C. To the cooled solution was added dropwise 48% aqueous sodium hydroxide (300 mL) with care to prevent the temperature from rising over 10° C., and then the solution was stirred at 10° C. or lower for 30 minutes. Then, the solution was warmed and stirred for one hour but not over 30° C., and further warmed and stirred at 40° C. for three hours. Purified water (1.0 L) was added thereto, and the solution was stirred at 40° C. for one more hour. The organic layer was separated, washed with purified water (1.0 L) twice. The solvent was removed in vacuo from the obtained solution to give the titled compound (262.1 g) as a colorless toluene solution (Content: 87.1%, Yield: 98.0%, UPLC Purity: >99%).
$^1$H-NMR (300 MHz, CDCl$_3$) δ: 2.45 (3H, s), 7.36 (2H, d, J 8.4 Hz), 7.80 (2H, d, J=8.4 Hz).

Reference Example 4

Synthesis of [$^2H_3$]methyl 2-nitrobenzenesulfonate

2-Nitrobenzenesulfonyl chloride (196 g) and $d_4$-methanol (30 mL) were dissolved in toluene (1.2 L), and the solution was cooled below −10° C. To the cooled solution was added dropwise 48% aqueous sodium hydroxide (180 mL) with care to prevent the temperature from rising over 5° C., and then the solution was stirred below 15° C. for three hours. Purified water (600 mL) was added thereto. The organic layer was separated, washed with purified water (300 mL) three times. About 900 mL of the solvent was removed in vacuo from the obtained solution, and the concentrated solution was stirred in an ice bath to precipitate a crystal. To the resulting suspension was added heptane (600 mL), and the suspension was warmed to room temperature, and then filtrated. The solid on the filter was washed with heptane (300 mL) and air-dried at 50° C. to give the titled compound as a pale yellow solid (120.2 g, Yield: 73.9%, UPLC Purity: >99%).
$^1$H-NMR (300 MHz, CDCl$_3$) δ: 7.75-7.87 (3H, m), 8.12-8.15 (1H, m).

Reference Example 5

Synthesis of [$^2H_3$]methyl 4-nitrobenzenesulfonate

4-Nitrobenzenesulfonyl chloride (12.6 g) and $d_4$-methanol (1.92 mL) were dissolved in toluene (77 mL), and the solution was cooled below −10° C. To the cooled solution was added dropwise 48% aqueous sodium hydroxide (11.5 mL) with care to prevent the temperature from rising over 5° C., and then the solution was stirred below 15° C. for three hours. Purified water (29 mL) was added thereto. The organic layer was separated, washed with purified water (19 mL) four times. About 60 mL of the solvent was removed in vacuo from the obtained solution, and the concentrated solution was stirred in an ice bath to precipitate a crystal. To the resulting suspension was added heptane (38 mL), and the suspension was warmed to room temperature, and then filtrated. The solid on the filter was washed with heptane (38 mL) and air-dried at 50° C. to give the titled compound as a pale yellow solid (6.64 g, Purity: 63.6%, UPLC Purity: >99%).

$^1$H-NMR (300 MHz, CDCl$_3$) δ: 8.11-8.15 (2H, m), 8.40-8.45 (2H, m).

Reference Example 6

Synthesis of (9S,13S,14S)-3-methoxymorphinan Hydrochloride

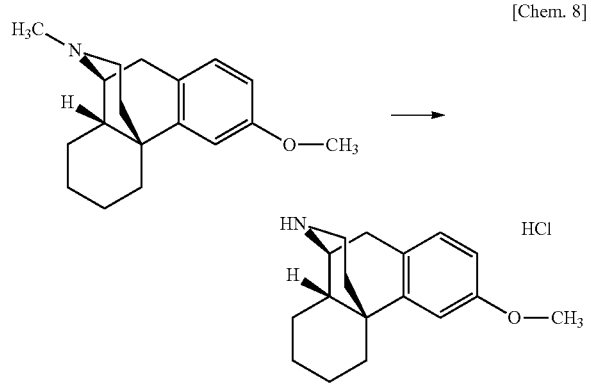

[Chem. 8]

(9S,13S,14S)-3-Methoxy-17-methylmorphinan (200 g) was dissolved in toluene (1.0 L), and 1-chloroethyl chloroformate (88 mL) was added to the toluene solution. The solution was stirred at room temperature for one hour. The solution was heated to 65° C., and then MeOH (200 mL) was added thereto. The solution was refluxed for an hour. The solution was cooled to room temperature, and then about 200 mL of the solvent was removed in vacuo from the solution. Toluene (400 mL) was added thereto, and about 400 mL of the solvent was removed from the diluted solution, and then toluene (200 mL) was added thereto, and about 200 mL of the solvent was removed from the diluted solution. 2-Propanol (20 mL) was added thereto, and the solution was stirred at 70° C. for an hour. The solution was cooled to room temperature and then filtrated. The solid on the filter was washed with toluene (600 mL) and air-dried at 60° C. overnight to give the titled compound as a white to pale yellow solid (182.1 g, Yield: 84.1%, UPLC Purity: >96%).

$^1$H-NMR (300 MHz, DMSO-d$_6$) δ: 0.89-0.96 (1H, m), 1.14 (1H, t, J=12.6 Hz), 1.25 (2H, t, J=12.6 Hz), 1.38-1.65 (4H, m), 1.76 (1H, dt, J=4.8 Hz, J=13.5 Hz), 1.92 (1H, d, J=12.6 Hz), 2.36-2.45 (2H, m), 2.96-3.15 (3H, m), 3.60-3.62 (1H, m), 3.73 (3H, s), 6.79-6.84 (2H, m), 7.11-7.14 (1H, m), 9.34 (2H, br).

Example 1

Synthesis of (9S,13S,14S)-3-methoxy-17-benzylmorphinan Oxalate

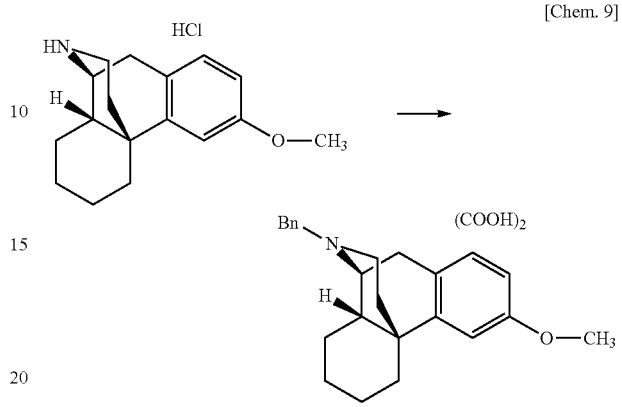

[Chem. 9]

Wherein Bn denotes benzyl group. The same applies hereinafter.

(9S,13S,14S)-3-Methoxymorphinan hydrochloride (50.0 g), potassium carbonate (51.7 g), and potassium iodide (2.82 g) were suspended in DMF (200 mL), and then benzyl chloride (19.8 mL) was added thereto. The suspension was heated to 60° C. and stirred for one hour at the same temperature. To the reaction mixture were added toluene (300 mL) and purified water (300 mL), and the organic layer was taken out of the mixture. The organic layer washed with purified water (300 mL), and the solvent was removed in vacuo from the organic layer. To the residue was added 2-propanol (400 mL) and the solution was heated to 70° C. To the solution was oxalic acid dihydrate (21.5 g), and the mixture was stirred for about 10 minutes. After confirming the precipitation of crystal, the mixture was stirred under reflux for one hour, and then cooled to room temperature. The mixture was ripened for about 30 minutes at the same temperature. The precipitated solid was collected on a filter, washed with 2-propanol (100 mL), and air-dried at 50° C. overnight to give the titled compound as a white to pale yellow solid (70.2 g, Yield: 94.4%, UPLC Purity: >99%).

$^1$H-NMR (300 MHz, DMSO-d$_6$) δ: 0.91-0.99 (1H, m), 1.11-1.60 (7H, m), 1.89 (1H, dt, J=4.2 Hz, J=13.2 Hz), 2.09 (1H, d, J=12.6 Hz), 2.41-2.53 (2H, m), 2.85-2.98 (2H, m), 3.27-3.33 (2H, m), 3.74 (3H, s), 4.31 (2H, s), 5.92 (2H, br), 6.81-6.84 (2H, m), 7.14-7.17 (1H, m), 7.41-7.46 (3H, m), 7.54-7.58 (2H, m).

Example 2

Synthesis of (9S,13S,14S)-3-hydroxy-17-benzylmorphinan Hydrobromide

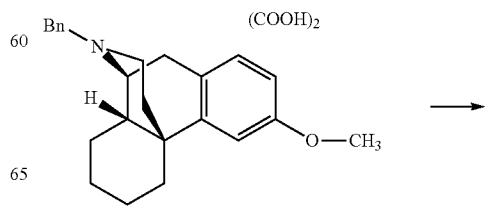

[Chem. 10]

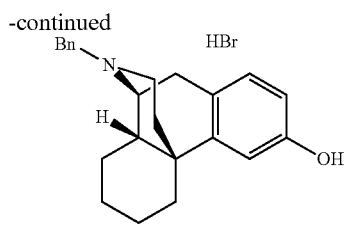

To (9S,13S,14S)-3-methoxy-17-benzylmorphinan oxalate (50.0 g) were added acetic acid (62.5 mL) and 48% aqueous hydrobromic acid (187.5 mL), and the mixture was heated at 110° C. or higher temperature, and stirred for one hour at the same temperature. Separately, a different vessel was charged with purified water (600 mL) and heated to 80° C. To the heated purified water was poured the above reaction mixture at 60° C. or higher temperature, together with purified water (300 mL) whose temperature is 60° C. or higher. The reaction mixture was cooled to room temperature, and the resulting precipitate was collected on a filter. The solid on the filter was washed with purified water (750 mL) before the pH of the filtrate became 6-7. The solid was air-dried at 60° C. to give the titled compound as a white to pale yellow solid (45.0 g, Yield: 95.1%, UPLC Purity: >99%).

$^1$H-NMR (300 MHz, DMSO-$d_6$) δ:0.85-0.99 (1H, m), 1.11-1.60 (7H, m), 1.82-1.91 (1H, m), 2.03-2.07 (1H, m), 2.10-2.45 (2H, m), 2.55-2.75 (2H, m), 2.80-2.95 (1H, m), 3.05-3.20 (1H, m), 4.44 (2H, d, J=4.8 Hz, major), 4.66 (2H, d, J=5.4 Hz, minor), 6.63-7.72 (2H, m), 6.96-6.99 (2H, m, minor), 7.05-7.08 (1H, m, major), 7.46-7.48 (3H, m), 7.62-7.63 (2H, m), 9.27 (1H, s), 9.43 (1H, br, minor), 9.57 (1H, br, major).

Synthesis of (9S,13S,14S)-3-[$^2$H$_3$]methoxy-17-[17,17,17-$^2$H$_3$]methylmorphinan

[Chem. 11]

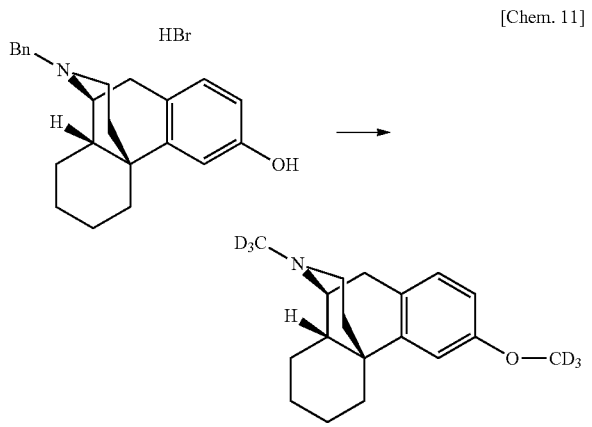

According to the following Examples 3-8, the titled compound was prepared by using each $d_3$-methylating agent.

Example 3

Synthesis by using [$^2$H$_3$]methyl Iodide (9S,13S,14S)-3-Hydroxy-17-benzylmorphinan hydrobromide (10.0 g) was suspended in DMF (100 mL). The suspension was cooled to 10° C., and then sodium tert-butoxide (4.87 g) was added thereto. The reaction mixture was cooled to 10° C. again, then [$^2$H$_3$]methyl iodide (1.65 mL) was added thereto, and the reaction mixture was stirred at 10-20° C. for one hour. To the reaction mixture were added toluene (80 mL) and purified water (100 mL), and the organic layer was taken out of the mixture. The organic layer washed with purified water (80 mL), and the solvent was removed in vacuo from the organic layer. The resulting oily compound was used in the next step without purification. To the obtained crude product were added sodium bicarbonate (0.41 g), [$^2$H$_3$]methyl iodide (1.8 mL), and acetonitrile (40 mL). The mixture was stirred at 50° C. for five hours, then [$^2$H$_3$]methyl iodide (0.45 mL) was further added to the reaction mixture, and the mixture was stirred at 50° C. for 3 more hours. The reaction mixture was cooled to room temperature, and then the inside of the reaction vessel was purged with nitrogen. Purified water (20 mL) was added to the reaction mixture, and the reaction mixture was refluxed for 30 minutes. The reaction mixture was cooled to room temperature, and then the inside of the reaction vessel was purged with nitrogen again. The obtained solution was used in the next step as the desired diastereomer mixture without further purification. To the crude solution comprising the product was added 5% Pd—C (0.5 g), and the mixture was stirred under hydrogen atmosphere at 50° C. for six hours. The reaction mixture was filtered through Celite, and washed with methanol (20 mL) and purified water (20 mL). Most of the organic solvent in the filtrate was removed in vacuo. To the residue was added methanol (20 mL), and the solution was heated to 50° C. To the solution was added dropwise an aqueous solution that 25% aqueous sodium hydroxide (4.6 mL) was diluted with purified water (20 mL) at 50-60° C. The reaction mixture was stirred at 50° C. for one hour, and cooled to room temperature. The obtained solid precipitate was collected on a filter, washed with a mixed solvent of methanol (20 mL) and purified water (40 mL), and air-dried at 60° C. to give the titled compound as a white solid (5.92 g, Total yield: 88.4%, UPLC Purity: >99.8%).

$^1$H-NMR (300 MHz, CDCl$_3$) δ: 1.10-1.19 (1H, m), 1.26-1.53 (6H, m), 1.62-1.83 (3H, m), 2.07 (1H, dt, J=3.3 Hz, J=12.0 Hz), 2.33-2.45 (2H, m), 2.58 (1H, dd, J=5.7 Hz, J=18.3 Hz), 2.78-2.81 (1H, m), 2.98 (1H, d, J=18.3 Hz), 6.69 (1H, dd, J=2.7 Hz, J=8.4 Hz), 6.80 (1H, d, J=2.7 Hz), 7.03 (1H, d, J=8.4 Hz).

Example 4

Synthesis by using [$^2$H$_3$]methyl Methanesulfonate (9S,13S,14S)-3-Hydroxy-17-benzylmorphinan hydrobromide (10.0 g) was suspended in DMF (60 mL). The suspension was cooled to 10° C., and then sodium tert-butoxide (4.87 g) was added thereto. The reaction mixture was cooled to 0° C. again, then [$^2$H$_3$]methyl methanesulfonate (3.0 g) was added thereto, and the reaction mixture was stirred at 0 to 10° C. for 3 hours. To the reaction mixture were added toluene (60 mL) and purified water (80 mL), and the organic layer was taken out of the mixture. The organic layer washed with purified water (60 mL), and the solvent was removed in vacuo from the organic layer. The resulting oily compound was used in the next step without purification. To the obtained crude product were added sodium bicarbonate (0.41 g), [$^2$H$_3$]methyl methanesulfonate (3.28 g), and acetonitrile (40 mL). The mixture was refluxed for 10 hours, then sodium bicarbonate (0.41 g) and purified water (20 mL)

were further added to the reaction mixture, and the mixture was stirred at 80° C. for one hour. The reaction mixture was cooled to room temperature, and then the obtained solution was used in the next step as the desired diastereomer mixture without further purification. To the crude solution comprising the product was added 5% Pd—C (0.5 g), and the mixture was stirred under hydrogen atmosphere at room temperature for 16 hours. The reaction mixture was filtered through Celite, and washed with methanol (20 mL) and purified water (20 mL). Most of the organic solvent in the filtrate was removed in vacuo. To the obtained solution were added toluene (40 mL), purified water (30 mL), and 25% aqueous sodium hydroxide (4.56 mL). The organic layer was taken out of the mixture. The organic layer washed with purified water (40 mL), and the solvent was removed in vacuo from the organic layer to give the titled compound as a white to pale yellow solid (6.58 g, Total yield: 98.2%, UPLC Purity: 87.1%).

Example 5

Synthesis by using [$^2$H$_3$]methyl Benzenesulfonate (9S,13S,14S)-3-Hydroxy-17-benzylmorphinan hydrobromide (10 g) was suspended in DMF (60 mL), and sodium tert-butoxide (4.87 g) was added thereto. The reaction mixture was cooled to 0° C., then [$^2$H$_3$]methyl benzenesulfonate (4.67 g) was added thereto, and the reaction mixture was stirred at 0° C. for two hours. To the reaction mixture were added toluene (50 mL) and purified water (60 mL), and the organic layer was taken out of the mixture. The organic layer washed with purified water (60 mL) twice, and the solvent was removed in vacuo from the organic layer. The resulting oily compound was used in the next step without purification. To the obtained crude product were sodium iodide (0.36 g), sodium bicarbonate (0.61 g), [$^2$H$_3$]methyl benzenesulfonate (5.10 g), and acetonitrile (40 mL). The mixture was stirred at 85° C. in an autoclave reactor for 4 hours. The reaction mixture was cooled to room temperature, and then the inside of the reactor was purged with nitrogen. Purified water (20 mL) was added to the reaction mixture, and the reaction mixture was stirred at 85° C. for two hours. The reaction mixture was cooled to room temperature, and then the inside of the reactor was purged with nitrogen again. The obtained solution was used in the next step as the desired diastereomer mixture without further purification. To the crude solution comprising the product was added 10% Pd—C (0.3 g), and the mixture was stirred under hydrogen atmosphere at 50° C. for 3 hours. The reaction mixture was filtered through Celite, and washed with methanol (10 mL) and purified water (10 mL). Most of the organic solvent in the filtrate was removed in vacuo. To the residue was added methanol (20 mL), and the solution was heated to 60° C. To the solution was added dropwise an aqueous solution that 25% aqueous sodium hydroxide (5.0 mL) was diluted with purified water (40 mL) at 50 to 60° C. The reaction mixture was stirred at 60° C. for 30 minutes, and cooled to room temperature. The obtained solid precipitate was collected on a filter, washed with a mixed solvent of methanol (4 mL) and purified water (16 mL), and air-dried at 50° C. to give the titled compound as a white solid (6.20 g, Total yield: 92.6%, UPLC Purity: >98%).

Example 6

Synthesis by using [$^2$H$_3$]methyl 4-methylbenzenesulfonate (9S,13S,14S)-3-Hydroxy-17-benzylmorphinan hydrobromide (20 g) was suspended in DMF (120 mL), and sodium tert-butoxide (9.74 g) was added thereto. The suspension was cooled to 0° C., and then a toluene solution of [$^2$H$_3$]methyl 4-methylbenzenesulfonate (10.83 g, content: 92.7%) was added thereto. The reaction mixture was stirred at 0° C. for 4 hours. To the reaction mixture were added toluene (100 mL) and purified water (120 mL), and the organic layer was taken out of the mixture. The organic layer washed with purified water (120 mL), and the solvent was removed in vacuo from the organic layer. The resulting oily compound was used in the next step without purification. To the obtained crude product were added sodium iodide (0.72 g), sodium bicarbonate (0.81 g), a toluene solution of [$^2$H$_3$]methyl 4-methylbenzenesulfonate (11.81 g, content: 92.7%), and acetonitrile (60 mL). The mixture was stirred at 85° C. in an autoclave reactor for 4 hours. The reaction mixture was cooled to room temperature, and then the inside of the reactor was purged with nitrogen. Purified water (20 mL) was added to the reaction mixture, and the reaction mixture was stirred at 85° C. for two hours. The reaction mixture was cooled to room temperature, and then the inside of the reactor was purged with nitrogen again. The obtained solution was used in the next step as the desired diastereomer mixture without further purification. To the crude solution comprising the product was added 10% Pd—C (0.6 g), and the mixture was stirred under hydrogen atmosphere at 50° C. for 5 hours. The reaction mixture was filtered through Celite, and washed with acetonitrile (20 mL) and purified water (20 mL). Most of the organic solvent in the filtrate was removed in vacuo. To the residue was added methanol (20 mL), and the solution was heated to 50° C. To the solution was added dropwise an aqueous solution that 25% aqueous sodium hydroxide (8.9 mL) was diluted with purified water (40 mL) at 50 to 60° C. The reaction mixture was stirred at 50° C. for one hour, and cooled to room temperature. The obtained solid precipitate was collected on a filter, washed with a mixed solvent of methanol (20 mL) and purified water (40 mL), and air-dried at 60° C. to give the titled compound as a white solid (13.24 g, Total yield: 98.9%, UPLC Purity: >99.8%).

Example 7

Synthesis by using [$^2$H$_3$]methyl 2-nitrobenzenesulfonate (9S,13S,14S)-3-Hydroxy-17-benzylmorphinan hydrobromide (20 g) was suspended in DMF (120 mL), and sodium tert-butoxide (9.74 g) was added thereto. The suspension was cooled to −10° C., and then [$^2$H$_3$]methyl 4-methylbenzenesulfonate (12.75 g) was added thereto. The reaction mixture was stirred at −10° C. for one hour. Then, additionally, sodium tert-butoxide (1.62 g) was added to the reaction mixture, and the reaction mixture was stirred at the same temperature for one hour. To the reaction mixture were added toluene (120 mL) and purified water (120 mL), and the organic layer was taken out of the mixture. The organic layer washed with purified water (120 mL), and the solvent was removed in vacuo from the organic layer. The resulting oily compound was used in the next step without purification. To the obtained crude product were added sodium bicarbonate (0.81 g), [$^2$H$_3$]methyl 4-methylbenzenesulfonate (11.69 g), and acetonitrile (40 mL). The mixture was stirred at 60° C. in an autoclave reactor for 3 hours. The reaction mixture was cooled to room temperature, and then purified water (40 mL) was added to the reaction mixture, and the reaction mixture was stirred at 80° C. for 3 hours. The reaction mixture was cooled to room temperature, and then the obtained solution was used in the next step as the desired diastereomer mixture without further purification. To the crude solution comprising the product was added 10% Pd—C (0.6 g), and the mixture was stirred under hydrogen atmosphere at room temperature for 2.5 hours. The reaction mixture was filtered through Celite, and washed with acetonitrile (40 mL). Most of the organic solvent in the filtrate was removed in vacuo. To the obtained solution were added toluene (80 mL), purified water (70 mL), and 25% aqueous sodium hydroxide (10 mL). The organic layer was taken out of the mixture. The organic layer washed with purified water (80 mL×3), and the solvent was removed in vacuo from the organic layer. To the residue was added methanol (20 mL), and the solution was heated to 60° C. Purified water (180 mL) was added to the reaction mixture, and the reaction mixture was stirred at 80° C. for 30 more minutes. The reaction mixture was cooled to room temperature. The obtained solid precipitate was collected on a filter, washed with a mixed solvent of methanol (10 mL) and purified water (90 mL), and air-dried at 50° C. to give the titled compound as a white solid (12.94 g, Total yield: 96.6%, UPLC Purity: >99.8%).

Example 8

Synthesis by using [$^2$H$_3$]methyl 4-nitrobenzenesulfonate (9S,13S,14S)-3-Hydroxy-17-benzylmorphinan hydrobromide (8.0 g) was suspended in DMF (48 mL), and sodium tert-butoxide (3.90 g) was added thereto. The suspension was cooled to 0° C., and then [$^2$H$_3$]methyl 4-nitrobenzenesulfonate (4.68 g) was added thereto. The reaction mixture was stirred at 0° C. for two hours. To the reaction mixture were added toluene (40 mL) and purified water (48 mL), and the organic layer was taken out of the mixture. The organic layer washed with purified water (48 mL×2), and the solvent was removed in vacuo from the organic layer. The resulting oily compound was used in the next step without purification. To the obtained crude product were added sodium iodide (0.29 g), sodium bicarbonate (0.49 g), [$^2$H$_3$]methyl 4-nitrobenzenesulfonate (5.10 g), and acetonitrile (32 mL). The mixture was stirred at 85° C. in an autoclave reactor for 4 hours. The reaction mixture was cooled to room temperature, and then the inside of the reactor was purged with nitrogen. Purified water (16 mL) was added to the reaction mixture, and the reaction mixture was stirred at 85° C. for one hour. The reaction mixture was cooled to room temperature, and then the inside of the reactor was purged with nitrogen again. The obtained solution was used in the next step as the desired diastereomer mixture without further purification. To the crude solution comprising the product was added 10% Pd—C (0.24 g), and the mixture was stirred under hydrogen atmosphere at 50° C. for 3 hours. The reaction mixture was filtered through Celite, and washed with methanol (8 mL) and purified water (8 mL). Most of the organic solvent in the filtrate was removed in vacuo. To the residue was added methanol (20 mL), and the solution was heated to 60° C. To the solution was added dropwise an aqueous solution that 25% aqueous sodium hydroxide (4.0 mL) was diluted with purified water (40 mL) at 50 to 60° C. The reaction mixture was stirred at 60° C. for one hour, and cooled to room temperature. The obtained solid precipitate was collected on a filter, washed with a mixed solvent of methanol (8 mL) and purified water (32 mL), and air-dried at 60° C. to give the titled compound as a white solid (4.98 g, Total yield: 93.0%, UPLC Purity: >98%).

Example 9

Synthesis of (9S,13S,14S)-3-hydroxy-17-benzylmorphinan

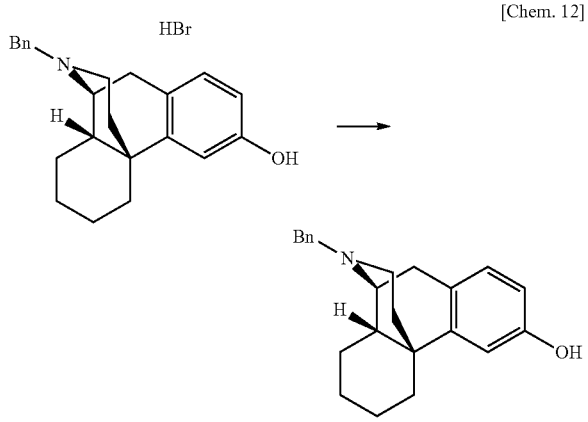

[Chem. 12]

(9S,13S,14S)-3-Hydroxy-17-benzylmorphinan hydrobromide (30.0 g) and sodium carbonate (8.44 g) were suspended in methanol (200 mL), and the suspension was refluxed for one hour. To the suspension was added purified water (300 mL) at 60° C. in 4 or 5 portions, and the reaction mixture was refluxed for one more hour. The reaction mixture was cooled to room temperature. The obtained solid precipitate was collected on a filter, washed with 30% methanol-water solution (v/v, 150 mL), and air-dried at 50° C. to give the titled compound as a white solid (23.6 g, Total yield: 99.2%, UPLC Purity: >99%).

$^1$H-NMR (300 MHz, CDCl$_3$) δ: 1.02-1.18 (1H, m), 1.20-1.40 (5H, m), 1.43-1.53 (1H, m), 1.56-1.78 (2H, m), 1.80-1.90 (1H, m), 2.12 (1H, dt, J=3.0 Hz, J=12.0 Hz), 2.20-2.30 (1H, m), 2.40-2.50 (1H, m), 2.59 (1H, dd, J=5.7 Hz, J=18.0 Hz), 2.85 (1H, dd, J=2.7 Hz, J=5.7 Hz), 2.98 (1H, d, J=18.0 Hz), 3.61 (1H, d, J=13.2 Hz), 3.72 (1H, d, J=13.2 Hz), 5.30 (1H, br), 6.61 (1H, dd, J=2.7 Hz, J=8.1 Hz), 6.70 (1H, d, J=2.7 Hz), 6.99 (1H, d, J=8.1 Hz), 7.22-7.37 (5H, m).

Example 10

Synthesis of (9S,13S,14S)-3-[$^2$H$_3$]methoxy-17-[17, 17,17-$^2$H$_3$]methylmorphinan

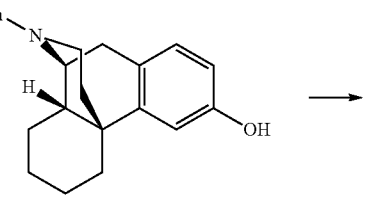

[Chem. 13]

-continued

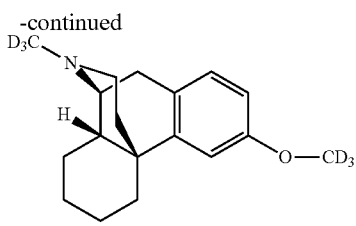

(9S,13S,14S)-3-Hydroxy-17-benzylmorphinan (10.0 g), a toluene solution of [$^2$H$_3$]methyl 4-methylbenzenesulfonate (13.45 g, content: 92.7%), and sodium bicarbonate (0.50 g) were suspended in acetonitrile (25 mL), and the suspension was refluxed for 4 hours. After the reaction, the reaction mixture was cooled to 0° C., to which 48% aqueous sodium hydroxide (3.0 g) was added. The reaction mixture was stirred at 0° C. for 16 hours and additionally at 80° C. for 4 hours, and then cooled to room temperature. To the obtained solution was added 10% Pd—C (0.6 g), and the mixture was stirred under hydrogen atmosphere at room temperature for 19 hours. The reaction mixture was filtered through Celite, and washed with acetonitrile (10 mL) and purified water (10 mL). Most of the organic solvent in the filtrate was removed in vacuo. To the residue was added toluene (40 mL), purified water (30 mL), and 25% aqueous sodium hydroxide (5.5 mL). The organic layer was separated, washed with purified water (30 mL). The solvent was removed in vacuo from the obtained organic layer. To the obtained residue was added methanol (20 mL), and the solution was heated to 60° C. Then, purified water (40 mL) was added thereto, and the solution was stirred at 60° C. for 30 more minutes. The solution was cooled to room temperature, and the obtained precipitate was collected on a filter and washed with a mixture of methanol (10 mL) and purified water (40 mL). The solid on the filter was air-dried at 50° C. to give the titled compound as a white solid (7.97 g, Total yield: 95.8%, UPLC Purity: >99.8%).

INDUSTRIAL APPLICABILITY

The present invention provides a useful method to mono-alkylate a piperidine nitrogen of a piperidine derivative with deuterated lower-alkyl without producing a by-product di-alkylated with deuterated lower-alkyl. In detail, the present invention makes it possible to prepare the isomer of dextromethorphan in which methyl group at the 3rd position or methyl groups at the 3rd and 17th positions are replaced by d$_3$-methyl group, with high quality and inexpensively.

The invention claimed is:

1. A method of mono-alkylating a piperidine nitrogen in a piperidine derivative with a deuterated lower-alkyl by protecting the piperidine nitrogen with an aralkyl protective group, lower-alkylating the piperidine nitrogen with a deuterated lower-alkyl agent under neutral or basic condition, and then deprotecting the aralkyl protective group,
wherein the piperidine derivative is a morphinan derivative selected from the group consisting of 3-methoxymorphinan, 3-methylmorphinan, 3-hydroxymorphinan, N-desmethyl form of drotebanol, and N-desmethyl form of sinomenin.

2. The method of claim 1, wherein the morphinan derivative is 3 methoxymorphinan.

3. The method of claim 1, wherein the mono-alkylation is mono-methylation or mono-ethylation, and the deuterated-lower-alkylating agent is deuterated-methylating agent or deuterated-ethylating agent.

4. The method of claim 1, wherein the mono-alkylation is mono-methylation, and the deuterated-lower-alkylating agent is [$^2$H$_3$]methyl methanesulfonate, [$^2$H$_3$]methyl benzenesulfonate, [$^2$H$_3$]methyl 4-methylbenzenesulfonate, [$^2$H$_3$]methyl 2-nitrobenzenesulfonate, [$^2$H$_3$]methyl 4-nitrobenzenesulfonate, di-[$^2$H$_3$]methyl sulfate, di-[$^2$H$_3$]methyl carbonate, [$^2$H$_3$]methyl trifluoromethanesulfonate, [$^2$H$_3$]methyl bromide, or [$^2$H$_3$]methyl iodide.

5. The method of claim 1, wherein the aralkyl protective group is a benzyl-derivative protective group.

6. The method of claim 5, wherein the benzyl-derivative protective group is benzyl protective group.

7. The method of claim 5, wherein the deprotection is to deprotect the benzyl-derivative protective group by hydrogenation.

8. The method of claim 1, wherein the basic condition is adjusted with sodium carbonate, cesium carbonate, potassium carbonate, sodium bicarbonate, potassium bicarbonate, sodium hydride, potassium hydride, sodium hydroxide, potassium hydroxide, sodium tert-butoxide, potassium tert-butoxide, alkyllithium, lithium amide, sodium methoxide, or tert-amine.

9. A method of preparing 3-(methoxy-d$_3$)-17-(methyl-d$_3$)-morphinan from 3-methoxymorphinan by the method of claim 2, wherein
the methoxy group at the 3rd position of the morphinan is transformed to hydroxy group under acidic condition or Lewis acidic condition after protecting the piperidine nitrogen with an aralkyl protective group, and
followed by the deuterated-lower-alkylation and the deprotection.

10. The method of claim 8, wherein the alkyllithium is selected from the group consisting of n-butyllithium, sec-butyllithium, tert-butyllithium, and n-hexyllithium.

11. The method of claim 8, wherein the lithium amide is lithium diisopropyl amide and/or lithium hexamethyldisilazide.

12. The method of claim 8, wherein the tert-amine is selected from the group consisting of trimethylamine, triethylamine, triisopropylamine, and diisopropylethylamine.

* * * * *